United States Patent
Bremner et al.

(10) Patent No.: US 12,013,385 B2
(45) Date of Patent: Jun. 18, 2024

(54) FLUID SENSING SYSTEMS AND METHODS

(71) Applicant: Cranfield University, Cranfield (GB)

(72) Inventors: James Andrew Bremner, Cranfield (GB); Thomas Kissinger, Cranfield (GB); Elizabeth Jane Hodgkinson, Cranfield (GB); Ralph Peter Tatam, Cranfield (GB)

(73) Assignee: Cranfield University, Cranfield (GB)

( * ) Notice: Subject to any disclaimer, the term of this patent is extended or adjusted under 35 U.S.C. 154(b) by 652 days.

(21) Appl. No.: 17/274,270

(22) PCT Filed: Sep. 3, 2019

(86) PCT No.: PCT/GB2019/052448
§ 371 (c)(1),
(2) Date: Mar. 8, 2021

(87) PCT Pub. No.: WO2020/049287
PCT Pub. Date: Mar. 12, 2020

(65) Prior Publication Data
US 2021/0349068 A1    Nov. 11, 2021

(30) Foreign Application Priority Data
Sep. 6, 2018  (GB) ..................................... 1814542

(51) Int. Cl.
*G01N 15/1434* (2024.01)
*G01D 5/353* (2006.01)
(Continued)

(52) U.S. Cl.
CPC ..... *G01N 33/0075* (2013.01); *G01D 5/35316* (2013.01); *G01N 15/1436* (2013.01);
(Continued)

(58) Field of Classification Search
CPC .................................................. G01N 15/1436
See application file for complete search history.

(56) References Cited

U.S. PATENT DOCUMENTS 9,541,426 B2 *  1/2017  Farhadiroushan .......................... G01D 5/35358
2002/0041379 A1  4/2002  Lin et al.
(Continued)

FOREIGN PATENT DOCUMENTS

GB       2284256 A       5/1995
GB       2568305 A  *   5/2019   ............. G01D 5/268
(Continued)

OTHER PUBLICATIONS

Zavrsnik, "Analysis of quasi-distributed optical sensors combining rf modulation with the FMCW method", Optical Engineering, 2000, vol. 39, No. 11, pp. 3053-3059.
(Continued)

*Primary Examiner* — Charlie Y Peng
(74) *Attorney, Agent, or Firm* — MacMillan, Sobanski & Todd, LLC

(57) ABSTRACT

An interferometric fluid sensing system includes: a laser; a plurality of first fibre portions arranged to receive laser light from the laser; a second fibre portion configured to provide a reference arm for the interferometric fluid sensing system; and a detector arranged to receive light from the first and second fibre portions, wherein the laser light that passes through a void of each first fibre portion is caused to interfere with light passing through the second fibre portion at or before reaching the detector, wherein each of the first fibre portions is arranged such that that light passing through the void of each first fibre portion travels from the laser to the detector over a different path length from the light passing through the voids of the other first fibre portions.

22 Claims, 12 Drawing Sheets

(51) Int. Cl.
*G01N 21/39* (2006.01)
*G01N 21/45* (2006.01)
*G01N 33/00* (2006.01)

(52) U.S. Cl.
CPC .............. *G01N 21/39* (2013.01); *G01N 21/45* (2013.01); *G01N 2021/391* (2013.01); *G01N 2021/451* (2013.01)

(56) References Cited

U.S. PATENT DOCUMENTS

2014/0336957 A1* 11/2014 Hanson ................ G01J 3/4338
                                                                  702/50
2017/0030830 A1   2/2017 Kapit et al.

FOREIGN PATENT DOCUMENTS

| GB | 2571575 | A | * | 9/2019 | ............ | G01B 11/18 |
|---|---|---|---|---|---|---|
| GB | 2576920 | A | * | 3/2020 | ............ | E21B 47/10 |
| JP | 2004361129 | | | 12/2004 | | |
| WO | 2004005973 | A2 | | 1/2004 | | |
| WO | 2008098380 | A1 | | 8/2008 | | |
| WO | WO-2010051553 | A1 | * | 5/2010 | ............ | G01M 3/047 |
| WO | 2012122336 | A1 | | 9/2012 | | |
| WO | 2017087792 | A1 | | 5/2017 | | |

OTHER PUBLICATIONS

Tomaszewska et al., "Frequency-multiplexed gas sensing using chirped laser molecular spectroscopy", Opto-Electronics Review, Science Direct, 2018, vol. 26, pp. 103-107.

Bremner, "Distributed gas sensing using microstructured optical fibres", Capture, retrieved from the internet: URL: https://cord.cranfield.ac.uk/articles/Distributed_gas_sensing_using_microstructured_optical_fibres/7223942/1, retrieved on Oct. 16, 2019.

Sakai et al., "Multiplexing of Optical Fiber Sensors Using a Frequency-Modulated Source and Gated Output", Journal of Lightwave Technology, 1987, vol. LT-5, No. 7, pp. 932-940.

Kissinger et al., "Range-resolved interferometric signal processing using sinusoidal optical frequency modulation", Optical Society of America, 2015, vol. 23, No. 7, pp. 9415-9431.

PCT International Search Report and Written Opinion, Application No. PCT/GB2019/052448, dated Oct. 24, 2019.

Intellectual Property Office Patents Act 1977: Search Report under Section 17(5), Application No. GB1814542.5, dated Feb. 28, 2019.

* cited by examiner

No gas in all gas cells ($P_1$, $P_2$, $P_3$)

No gas in cell $P_2$, No gas in cells $P_1$ and $P_3$

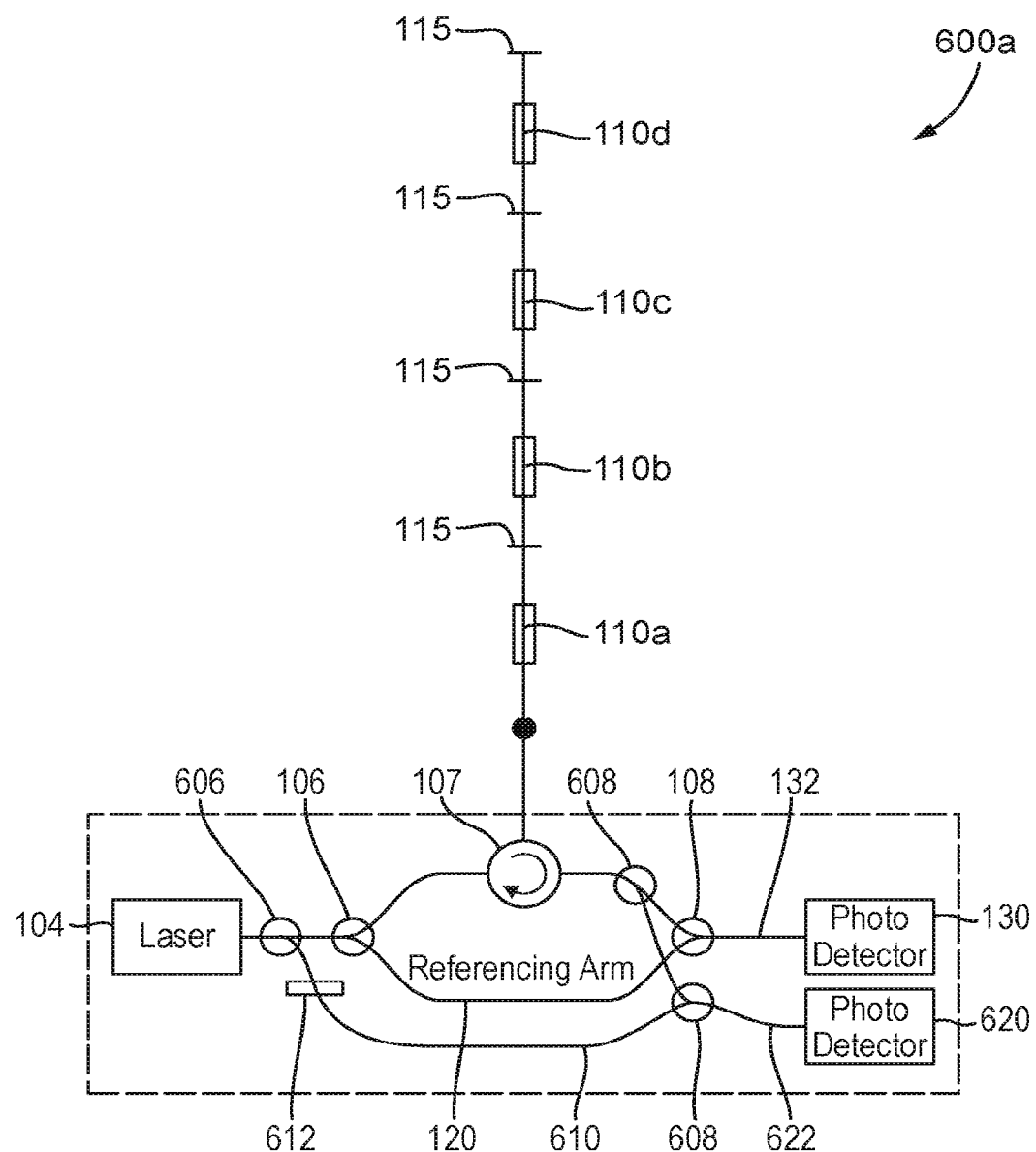

3 Gas cells $P_1$, $P_2$, $P_3$ at different times in the ramp $t_1$ and $t_2$ without preshaping 3 Gas cells $P_1$, $P_2$, $P_3$ at different times in the ramp $t_1$ and $t_2$ with preshaping

FLUID SENSING SYSTEMS AND METHODS

TECHNICAL FIELD

The present disclosure relates to interferometric fluid sensing systems and is particularly, although not exclusively, concerned with interferometric fluid sensing systems with improved coverage and/or resolution.

BACKGROUND

Different types of gas sensors are known for use along pipelines and in offshore oil and gas rigs for detecting the presence of gas clouds resulting from gas leaks. Typically, such gas sensors comprise pellistors, semiconductor gas sensors or electrochemical devices.

In areas where sensors are provided, they may be installed with a spacing of no more than 5 m between sensors. This is achieved by placing a number of standalone sensors at intervals of 5 m that are individually addressed, or by installing a multiplexed system of sensors.

Due to the large number of sensors that are required when spacing the gas sensors 5 m apart, and the complications associated with installing, calibrating and maintaining the sensors, installation of sensors is often prioritised to locations where the risk of gas leakage is greatest and/or where the consequences may be greatest, for example to personnel. The use of point sensors also has the disadvantage that, even with a distance between sensors of only 5 m, gas leaks may be missed, depending on the wind conditions.

It is desirable to provide an improved gas sensing system that increases the practicality of installing gas sensors at suitable intervals in each area of interest.

STATEMENTS OF INVENTION

According to an aspect of the present disclosure, there is provided an interferometric fluid sensing system comprising:
a laser;
a plurality of first fibre portions arranged to receive laser light from the laser, wherein each of the first fibre portions is associated with a corresponding void (e.g. space) into which fluid (such as a gas or liquid) from the environment around the corresponding first fibre portion is free to enter, wherein the first fibre portions are configured such that at least a portion of the laser light received by each first fibre portion interacts with the fluid in the corresponding void (e.g. with the laser light passing through and/or extending into the void);
a second fibre portion configured to provide a reference arm for the interferometric fluid sensing system; and
a detector arranged to receive light from the first and second fibre portions, wherein the system is configured such that the laser light that passes through each first fibre portion is caused to interfere with the light passing through the second fibre portion at or before reaching the detector, wherein each of the first fibre portions is arranged such that that light passing through each first fibre portion travels from the laser to the detector over a different path length from light passing through the other first fibre portions, wherein the system is configured such that the wavelength of light provided by the laser varies with time according to a modulated function, the modulated function comprising a first function, which varies through a range of wavelengths, e.g. according to a ramp or saw tooth wave form, modulated by a second, cyclical, e.g. sinusoidal, carrier function. The modulated function may comprise a cyclically modulated ramp or saw tooth function.

The first function may cause the laser to vary through the range of wavelengths at a first frequency. The frequency of the second function, e.g. a second frequency, may be different from, e.g. greater than, the first frequency. For example, the first frequency may be between 1 Hz and 10 Hz and the second frequency may be between 10 kHz and 100 kHz. An amplitude of the cyclical modulation may be less than the range of wavelengths through which the wave length is varied, e.g. according to the first function.

The range through which the wavelength of laser light varies, e.g. according to the first function, may include a value at which light is absorbed by a fluid to be detected.

The second fibre portion may be arranged between the laser and the detector in parallel with the plurality of first fibre portions. Alternatively, the second fibre portion may be arranged in series with the first fibre portions. For example, the first and second fibre portions may be arranged in series with each other.

The first fibre portions may be arranged in series with one another. The first fibre portions may be associated with, e.g. comprise, a partial reflector or a fibre boundary configured to reflect a portion of the light that has passed through the first fibre portion.

Each of the first fibre portions may comprise the corresponding void. The void may be provided within the first fibre portion. The first fibre portions may each comprise one or more openings that allows fluid from the environment around the first fibre portion to enter the void. The first fibre portion may continue to guide the light through the void. Alternatively, each of the first fibre portions may be coupled to a corresponding free space void, e.g. adjacent to the first fibre portion. Light may be coupled from the first fibre portion into the free space void, e.g. without the light being guided through the void by the first fibre portion.

The voids of the first fibre portions may be equally spaced apart from one another along the length of the series arrangement of the first fibre portions. For example, the voids of the first fibre portions may be spaced apart from one another along the length of the series arrangement of the first fibre portions by approximately 1 m or more. Additionally or alternatively, the partial reflectors or fibre boundaries of the first fibre portions may be equally spaced apart from one another along the length of the series arrangement of first fibre portions, e.g. by approximately 1 m or more. Alternatively, one or more of the voids and/or reflectors or fibre boundaries may be spaced apart along the length of the series arrangement of the first fibre portions by different distances to the other voids and/or reflectors or fibre boundaries, e.g. by less than 1 m.

The first fibre portions may be arranged in parallel with one another between the laser and the detector. The different branches of the parallel arrangements of first fibre portions may comprise different lengths of optical fibre, such that a path length of light passing through a particular branch is different to that of the light passing through the other branches.

The first fibre portions may be arranged in such a way as to combine sections of first fibre portions both in parallel and in series. There may be a branched network of first fibre portions branching from a main fibre at successive locations.

The laser may comprise a laser diode, e.g. an injection laser diode. The wavelength of the laser light produced by the laser diode may be modulated by varying an injection current supplied to the laser over time, e.g. by varying the current supplied to the laser according to a modulated, e.g. cyclically modulated, ramp or saw tooth function. The modulated function according to which the current is supplied to the laser may vary through a range of currents corresponding to the range of wavelengths.

The current supplied to the laser may be controlled such that an amplitude of cyclical variations in the current varies as the current supplied varies between minimum and maximum values of current. For example, the amplitude of the cyclical variations in the current may be increased as the current is increased between the minimum and maximum values. Alternatively, the amplitude of the cyclical variations in the current may be reduced as the current is increased between the minimum and maximum values. In this way, the amplitude of the cyclical variations in the wavelength of the light supplied by the laser may be substantially constant, e.g. as the wavelength varies between minimum and maximum wavelengths.

The system may further comprise a third fibre portion. The third fibre portion may be configured to provide a further reference arm of the interferometric fluid sensing system. The system may comprise a further detector arranged to receive light from the first and third fibre portions. The system may be configured such that the laser light that passes through each first fibre portion is caused to interfere with the light passing through the third fibre portion at or before reaching the further detector. The system may be configured such that light passing through the third fibre portion is polarised orthogonally to the light passing through the second fibre portion. For example, the system may comprise a polarisation controller or a device, such as a wave plate, configured to change the polarisation of light passing through the second and/or third fibre portions.

The system may further comprise a controller configured to process a signal received by one or more detectors (e.g. the detector and/or further detector) using a range-resolved interferometry technique, in order to distinguish between the portions of the signal corresponding to light that has passed through each of the first fibre portions, e.g. based on the optical path length difference at which interference occurs between light passing through the first and second fibre portions.

The controller may be configured to process signals received at the detector and the further detector in order to compensate for a polarisation inducing signal fading effect. The laser may be a low power laser. For example, a power coupled from the laser into the fibre portions may be less than 35 mW.

The system may further comprise a length of optical fibre arranged between the laser and the first optical fibre portions. The laser and detector may be provided in an interferometric interrogation unit, e.g. within a common housing of the interrogation unit. The first fibre portions may be optically coupled to the interrogation unit, e.g. by the length of optical fibre. The second fibre portion and/or the third fibre portion may be provided within the interferometric interrogation unit. The interferometric interrogation unit may further comprise an optical circulator or coupler configured to direct light from the laser to the first fibre portions and direct light from the first fibre portions to the detector.

According to another aspect of the present disclosure, there is provided an interferometric fluid detection method, the method comprising:

generating laser light, such that the wavelength of the laser light varies according to a modulated function, the modulated function comprising a first function, which varies through a range of wavelengths, modulated by a second, cyclical carrier function, e.g. such that the wave length of light varies with time through a range of wavelengths, and wherein a cyclical wavelength modulation is superimposed onto the variation of wave length;

supplying the modulated laser light to:
a plurality of first fibre portions, wherein each of the first fibre portions is associated with a corresponding void (e.g. space) into which fluid (such as a gas or liquid) from the environment around the corresponding first fibre portion is free to enter, wherein the first fibre portions are configured such that at least a portion of the laser light received by each first fibre portion interacts with fluid in the corresponding void; and
a second fibre portion configured to provide a reference arm;

causing the laser light that passes through each first fibre portion is to interfere with the light passing through the second fibre portion; and detecting the interferometric signal resulting from the interference of light from the first and second fibre portions using a detector.

The method may further comprise processing the interferometric signal using a range-resolved interferometry technique, in order to distinguish between the signals corresponding to light that has passed through each of the first fibre portions.

The laser light may be supplied by a laser diode. Modulating the wavelength of the laser light may comprise varying a current supplied to the laser diode. The current supplied to the laser diode may be varied with time according to a modulated function, the modulated function comprising a first function, which varies through a range of currents, modulated by a second, cyclical carrier function. In other words, the current supplied may be varied through a range of currents, and a cyclical current modulation may be superimposed onto the variation of current.

The current may be varied such that the magnitude of variations in current due to the cyclical modulation of the current changes as the current is varied through the range of currents. In this way, an amplitude in the cyclical modulation of laser wavelengths produced by the laser diode may remain substantially constant as the wavelength varies over the range of wavelengths.

The method may comprise supplying the modulated laser light to a third fibre portion to provide a further reference arm. The method may further comprise arranging, e.g. controlling, the polarisation of the laser light supplied to the second and/or third fibre portions such that the polarisation of light passing through the third fibre portion is orthogonal to the laser light passing through the second fibre portion.

The method may comprise causing the laser light that passes through each first fibre portion to interfere with the light passing through the third fibre portion. The method may further comprise detecting the interferometric signal resulting from the interference of the light from the first and third fibre portions using a further detector.

The method may further comprise processing the interferometric signal from the detector and further detector to compensate for a polarisation induced signal fading effect.

The method may further comprise determining whether a fluid is present in the void of a particular first fibre portions based on an intensity and/or interferometric phase of a portion of the interferometric signal corresponding to light that has passed through the particular first fibre portion.

To avoid unnecessary duplication of effort and repetition of text in the specification, certain features are described in relation to only one or several aspects or embodiments of the invention. However, it is to be understood that, where it is technically possible, features described in relation to any aspect or embodiment of the invention may also be used with any other aspect or embodiment of the invention.

BRIEF DESCRIPTION OF THE DRAWINGS

For a better understanding of the present invention, and to show more clearly how it may be carried into effect, reference will now be made, by way of example, to the accompanying drawings, in which:

FIGS. 6a and 6b are schematic views of other interferometric fluid sensing systems, according to arrangements of the present disclosure;

FIGS. 8a and 8b are graphs that are useful for understanding the effect of current pre-shaping on the frequency spectrum of an interferometric signal.

DETAILED DESCRIPTION

Figure 1:
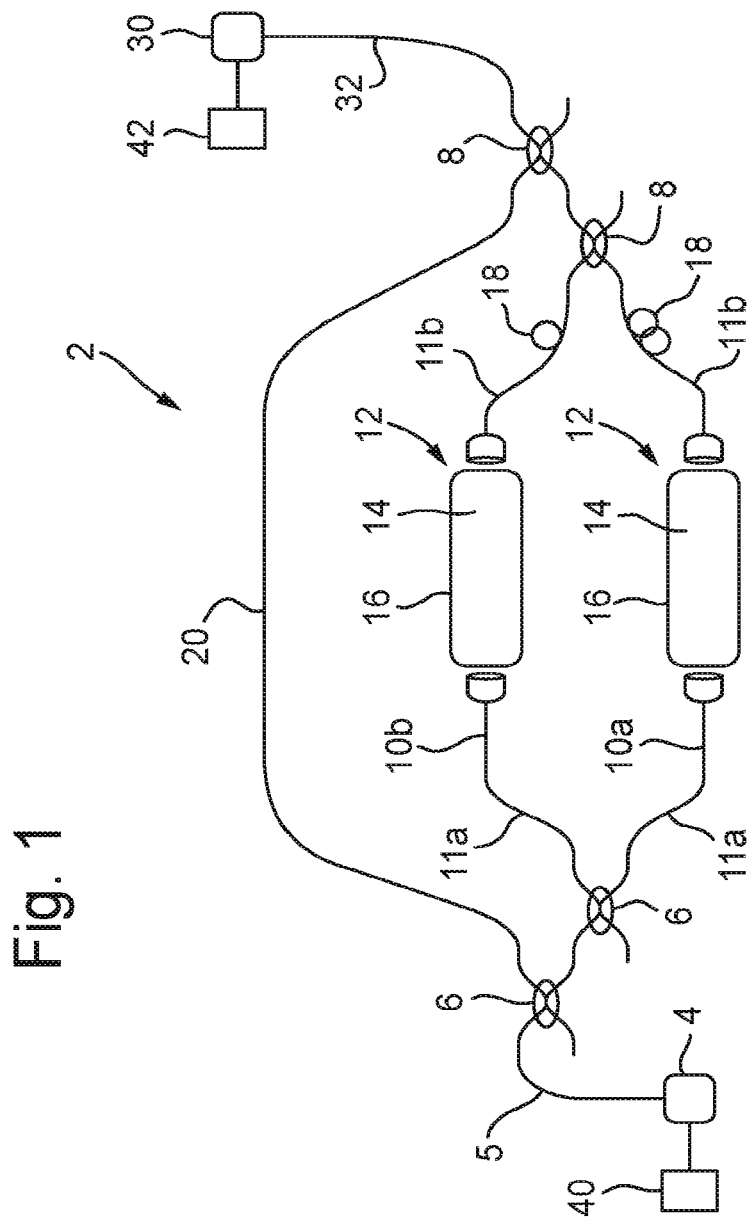
FIG. 1 is a schematic view of an interferometric fluid sensing system, according to arrangements of the present disclosure.

With reference to FIG. 1, an interferometric fluid, e.g. gas or liquid, sensing system 2, according to arrangements of the present disclosure, comprises a laser 4, a plurality of fluid, e.g. gas or liquid, detection fibre portions 10a, 10b arranged to receive laser light from the laser 4, and a detector 30 for sensing the light that has passed through the fluid detection fibre portions 10a, 10b.

The fluid detection fibre portions 10a, 10b are each associated with a void 14. In the particular example shown, each fluid detection fibre portion 10a, 10b comprises a void 14 having an opening 16 that allows fluid (such as a gas or liquid) in an environment around the corresponding fluid detection fibre portion 10a, 10b to enter the void 14. The fluid detection fibre portions 10a, 10b are configured such that the laser light, e.g. at least a portion of the light, received by the fluid detection fibre portions 10a, 10b is passed through and/or interacts with the respective voids 14 and any fluid present within the voids 14. In the arrangement shown in FIG. 1, two fluid detection fibre portions 10a, 10b are provided. However in other arrangements any desirable number of fluid detection fibre portions may be provided in the interferometric fluid sensing system 2.

In the arrangement shown in FIG. 1, the fluid detection fibre portions 10a, 10b comprise fluid cells 12, which define chambers forming the voids 14. Portions of optical fibre 11a, 11b are optically connected to either side of the fluid cell 12 in order to pass laser light through the fluid cell 12. In other arrangements, the voids 14 may be formed by hollow portions of optical fibre or any other structure that enables fluid within the voids 14 to be placed within the path of light passing through the fluid detection fibre portions 10a, 10b. By way of example, the fluid detection fibre portions 10a, 10b may comprise gas cells and/or hollow-core fibres (such as hollow-core photonic crystal fibres, e.g. where the fibre itself both forms the void and simultaneously guides the light). In another arrangement, the fluid detection fibre portions 10a, 10b may comprise a suspended core fibre, which may consist of a (e.g. thin) solid fibre core suspended in a cavity, where light can interact with the fluid in the cavity through evanescent interactions. An evanescent field describes the (e.g. small) fraction of the guided light field that travels in the region around the core in addition to the light that travels within the solid (e.g. glass) core. The evanescent light can thus interact with the fluid. In a further arrangement, each of the first fibre portions may be coupled to a corresponding free space void, e.g. adjacent to the first fibre portion. Light may be coupled from the first fibre portion into the free space void, e.g. without the light necessarily being guided through the void by the first fibre portion.

The interferometric fluid sensing system 2 further comprises a reference fibre portion 20, which is configured to form a reference arm of the interferometric system 2. As depicted in FIG. 1, the reference fibre portion 20 may not comprise a void. However, in other arrangements, the reference fibre portion 20 may be similar to the fluid detection fibre portion 10a, 10b, and may comprise a void. For example, when a particular fibre portion that comprises a void is acting as a reference arm of the interferometric system 2, e.g. as the reference fibre portion 20, the reference fibre portion 20 may be placed in an environment containing no fluid or a known fluid, e.g. a fluid that is not to be detected by the interferometric fluid sensing system 2 or a fluid that is to be detected by the interferometric fluid sensing system, at a fixed concentration that substantially does not hamper the performance of the system.

The interferometric fluid sensing system 2 further comprises a plurality of first optical couplers 6 for optically coupling the fluid detection fibre portions 10a, 10b and reference fibre portion 20 to the laser 4. For example, the first optical couplers 6 may couple the fluid detection fibre portions 10a, 10b and reference fibre portion 20 together and to an optical fibre 5 coupled to the laser 4. The interferometric fluid sensing system 2 further comprises a plurality of second optical couplers 8 for optically coupling the fluid detection fibre portions 10a, 10b and the reference fibre portion 20 to the detector 30. For example, the second optical couplers 8 may be arranged to optically couple the fluid detection fibre portions 10a, 10b and the reference fibre portion 20 together, and to an optical fibre 32 coupled to the detector 30.

The first and second optical couplers 6, 8 are arranged such that laser light from the laser 4 is separated, by the first optical couplers 6, into portions that pass through respective ones of the fluid detection fibre portions 10a, 10b and reference fibre portion 20 before being combined, by the second optical couplers 8, before reaching the detector 30. In this way, light passing through each of the fluid detection fibre portions 10*a*, 10*b* is caused to interfere with light passing through the reference fibre portion 20 at or before reaching the detector 30.

As depicted in FIG. 1, the first and second optical couplers 6, 8 may comprise two inputs and two outputs. In this case one of the inputs of each of the first optical couplers 6 may be disconnected and one of the outputs of each of the second optical couplers 8 may be disconnected. Alternatively, the optical couplers may have any other suitable numbers of inputs and outputs in order to split and combine portion of the laser light as desired. Accordingly, different numbers of optical couplers may be provided as appropriate. For example in one arrangement, a single first optical coupler having one input and three outputs may be provided to separate the light from the laser to pass through the fluid detection fibre portions 10*a*, 10*b* and reference fibre portion 20.

The detector 30 may comprise any sensor capable of detecting the interferometric signal from the fluid detection fibre portions 10*a*, 10*b* and reference fibre portion 20. For example, the detector 30 may comprise a photo detector.

The interferometric fluid sensing system 2 further comprises a laser controller 40 configured to control the operation of the laser to provide light to the fluid detection fibre portions 10*a*, 10*b* and reference fibre portion 20. The interferometric fluid sensing system 2 may further comprise a detector controller 42 configured to control the operation of the detector 30 to detect and process the interferometric signal received by the detector 30.

The detector controller 42 may be a separate controller to the laser controller 40. Alternatively, the functions of the laser controller 40 and the detector controller 42 may be performed by the same controller, e.g. by one or more modules of a system controller.

The interferometric fluid sensing system 2 is configured such that portions of the laser light that pass through the voids 14 of each of the fluid detection fibre portions 10*a*, 10*b* travel over different path lengths to one another between the laser 4 and the detector 30. As shown in FIG. 1, each fluid detection fibre portion 10*a*, 10*b* may comprise a length of optical fibre 18 having a different length to lengths of the optical fibres provided in the other fluid detection fibre portions. For example, one of the fluid detection fibre portions 10*b* may comprise a length of optical fibre 18 having a length of 1 m and another of the fluid detection fibre portions 10*a* may comprise a length of optical fibre having a length of 3 m. As depicted in FIG. 1, the lengths of optical fibre 18 may be provided between the void 14 in the fluid detection fibre portion 10*a*, 10*b* and one of the second optical couplers 8, e.g. the second optical coupler that couples the fluid detection fibre portion to another fibre portion and/or to the optical fibre 32 coupled to the detector 30. Alternatively, the length of optical fibre 18 may be provided between one of the first optical couplers 6 and the void 14.

By configuring the interferometric fluid sensing system 2, such that portions of the laser light that pass through the voids 14 of each of the fluid detection fibre portions 10*a*, 10*b* travel over different path lengths from one another between the laser 4 and detector 30, interference between the light passing through each of the fluid detection fibre portions 10*a*, 10*b* and the light passing through the reference fibre portion 20 occurs with a different Optical Path-length Difference (OPD) compared to the interference between light passing through the other fluid detection fibre portions 10*a*, 10*b* and light passing through the reference fibre portion 20. This allows the portions of the interferometric signal relating to each of the fluid detection fibre portions 10*a*, 10*b* to be individually resolved, as described below.

Range-Resolved Interferometry (RRI) is a technique that allows portions of an interferometric signal from a plurality of interferometers to be distinguished from one another by their optical path length difference, e.g. the difference in the distances travelled by the light passing along each arm of the interferometers that have produced the interferometric signal. This allows simultaneous determination of the intensity and interferometric phases of multiple interferometers, the signal from which have been separated based on their differing OPDs.

As described above, the distance travelled by the light passing through the voids 14 in each of the fluid detection fibre portions 10*a*, 10*b* is different, and hence, the OPD with which the light from each fluid detection fibre portion 10*a*, 10*b* interferes with the light passing through the reference fibre portion 20 is different. This allows the portions of the interferometric signal corresponding to each of the different fluid detection fibre portions 10*a*, 10*b* to be separately identified within the interferometric signal, regardless of whether the same or different types and/or amounts of fluid are present in the different voids 14.

The RRI technique is performed by modulating the wavelength (or frequency) of laser light produced by the laser 4. The wavelength of the laser light may be modulated using a linear modulation function, such as a triangular or saw tooth modulation function. Alternatively, as depicted in the top frame of FIG. 2*a*, the wavelength of the laser light may be modulated using a cyclical, e.g. sinusoidal, modulation function $F_1$. Using a sinusoidal modulation function may reduce the complexity of the system due to a reduced number of harmonic frequency components within the modulation function.

Figure 2A:
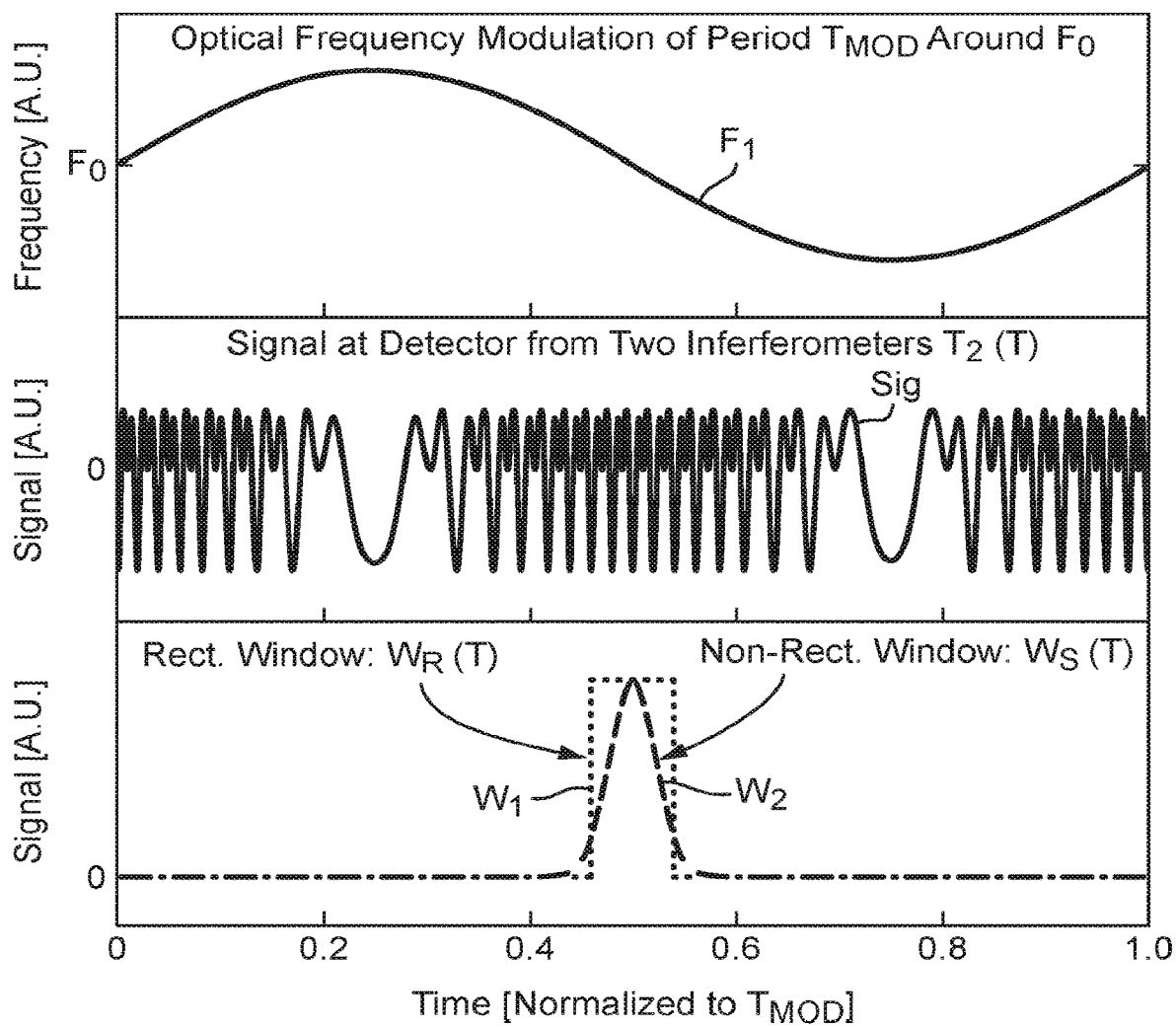
FIGS. 2a and 2b are graphs that are useful for understanding range resolved interferometry.

The middle frame of FIG. 2*a* depicts an example of an interferometric signal Sig received at a common detector from two interferometers that have been provided with laser light modulated using the modulation function $F_1$. Each of the interferometers is configured to cause interference of the laser light over a different OPD.

The detected interferometric signal Sig may be multiplied by a window function. Two examples of windows functions $W_1$ and $W_2$ are shown in the bottom frame of FIG. 2*a*. The first window function $W_1$ is a square function and the second window function $W_2$ is a smooth window function, such as a Gaussian window function. It is also envisaged that other window functions may be used as desirable.

Figure 2B:
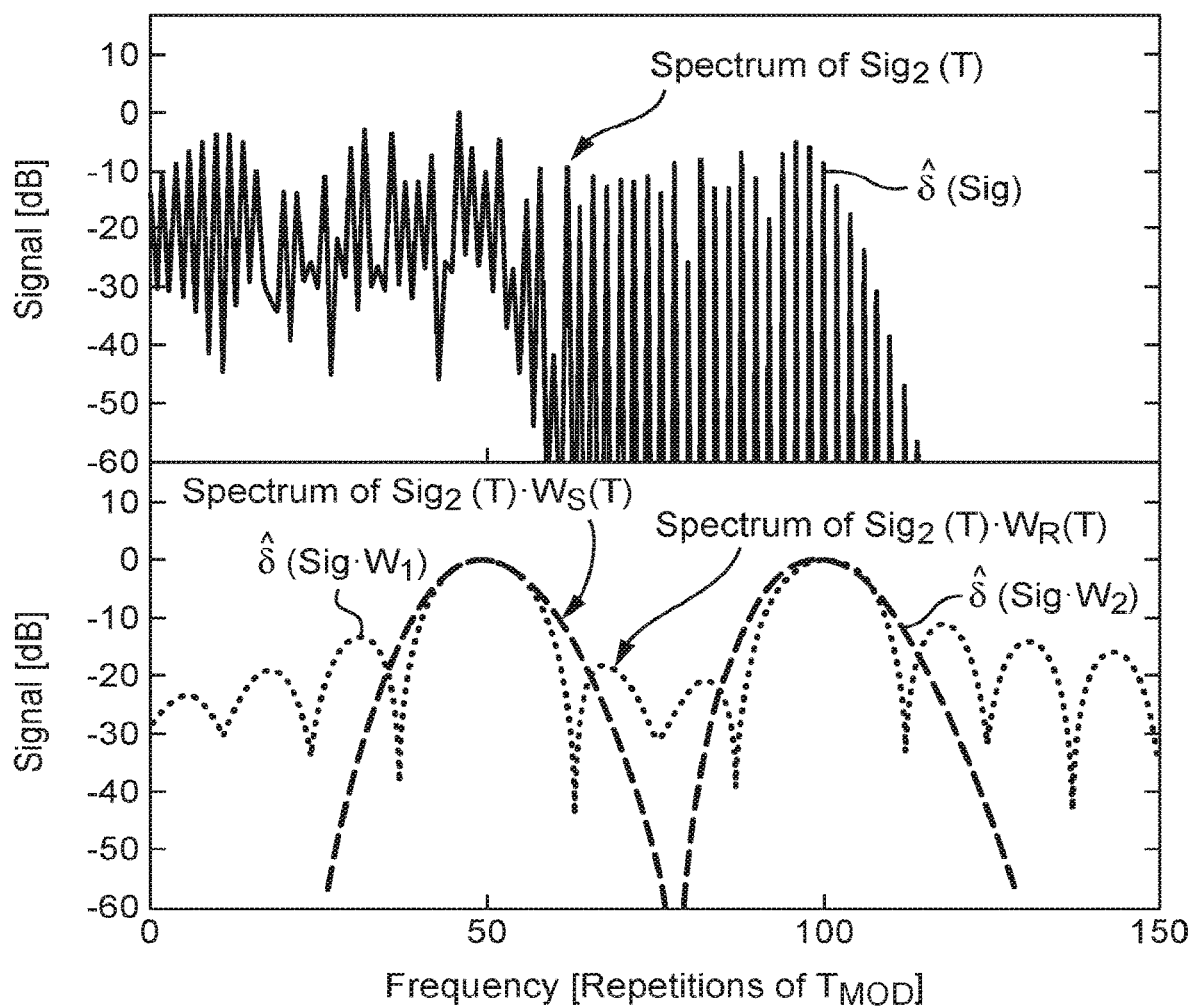

With reference to FIG. 2*b*, in order to determine the relative OPDs of the two interferometers, the detected interferometric signal is transformed into the frequency domain, e.g. by performing a Fourier transform ($\hat{\delta}$) of the interferometric signal after multiplication with the window function $W_1$ or $W_2$. Due to the modulation of the laser light sent to the interferometers, the positions of peaks in the frequency spectrum of the interferometric signal correspond to the OPDs of the interferometers.

The top frame of FIG. 2*b* shows a frequency spectrum $\hat{\delta}(\text{Sig})$ of the interferometric signal and the bottom frame shows the frequency spectrums $\hat{\delta}(\text{Sig} \cdot W_1)$ and $\hat{\delta}(\text{Sig} \cdot W_2)$ of the interferometric signals multiplied by the window function $W_1$ and $W_2$ respectively. As shown, when the smooth window function $W_2$ is applied to the interferometric signal, the peaks in corresponding frequency spectrum may be more distinct from one another with less interference from side lobes. In the frequency spectrum $\hat{\delta}(\text{Sig} \cdot W_2)$, two peaks are present, the frequencies of the peaks corresponding to the OPDs of the two interferometers.

The portions of the interferometric signal at the frequency of each of the peaks in the frequency spectrum can be extracted from the interferometric signal and intensity and interferometric phase information can be determined separately for each extracted portion of the signal. When the OPD of a particular interferometer is approximately known, e.g. after the interferometric system has been calibrated, the portion of the interferometric signal corresponding to the particular interferometer can be extracted by multiplying the interferometric signal from multiple interferometers where the smooth window function has been applied by the real and imaginary parts of a notional interferometric signal expected for an interferometer having that OPD. The intensity and interferometric phase can then be determined by the complex amplitude and phase, respectively, of the described real and imaginary signals.

Figure 3:
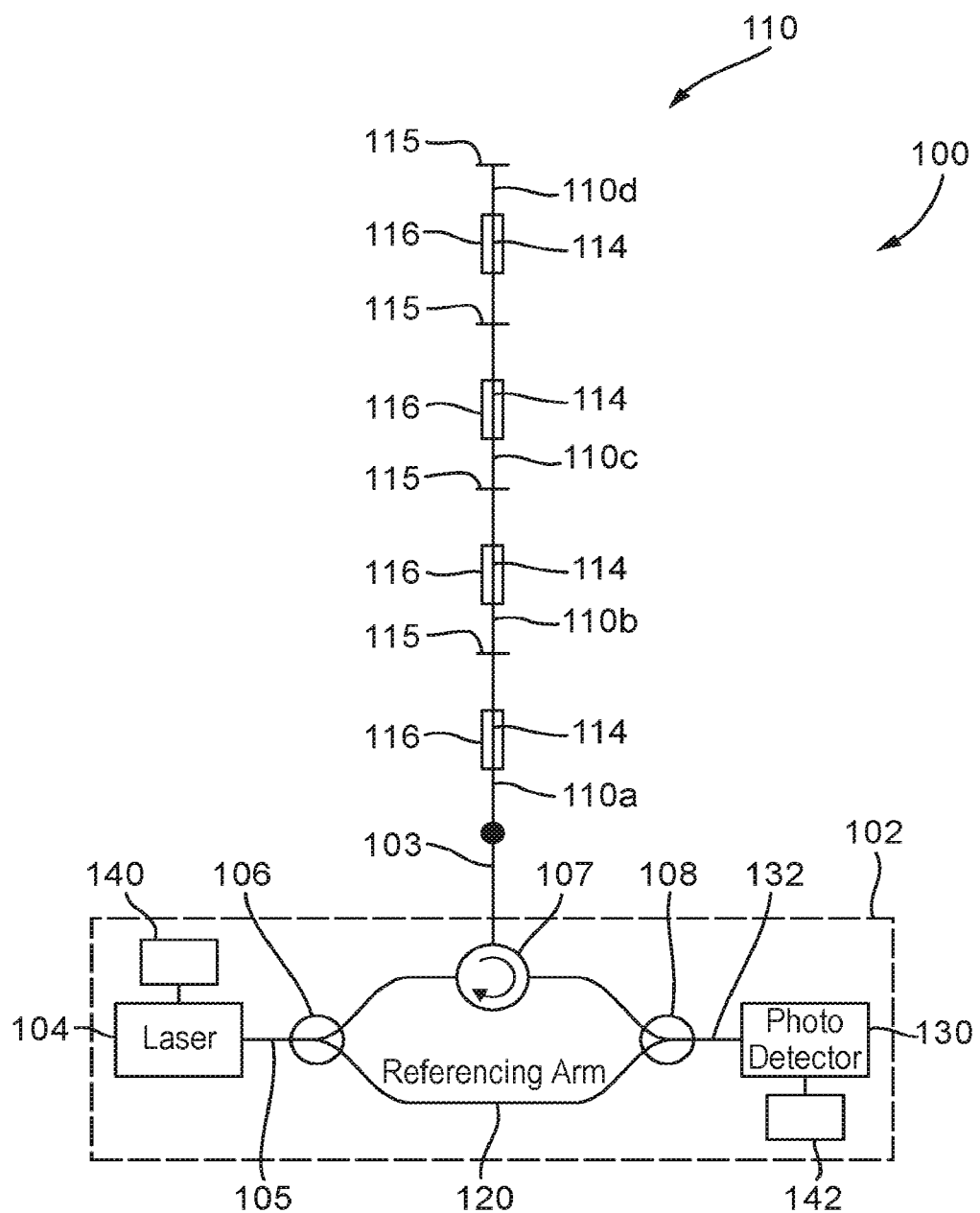
FIG. 3 is a schematic view of another interferometric fluid sensing system, according to arrangements of the present disclosure.

In the arrangement shown in FIG. 1, the fluid detection fibre portions 10a, 10b are arranged in parallel with one another between the laser 4 and the detector 30. However, with reference to FIG. 3, in an interferometric fluid sensing system 100 according to another arrangement of the present disclosure, fluid detection fibre portions 110a, 110b, 110c, 110d are coupled together to form a series arrangement 110 of fluid detection fibre portions. (The fluid detection fibre portions 110a, 110b, 110c, 110d may otherwise correspond to the fluid detection fibre portions 10a, 10b described above.) In FIG. 3, four fluid detection fibre portions are provided in series with one another. However in other arrangements, any other desirable number of fluid detection fibre portions may be provided. For example, the interferometric fluid sensing system 100 may comprise two, three, four or more than four fluid detection fibre portions arranged in series with each other. Furthermore, additional series arrangements of fluid detection fibre portions may be provided within the interferometric fluid sensing system 100, which may be arranged in parallel with one another.

As shown in FIG. 3, the interferometric fluid sensing system 100 comprises an optical circulator 107. The optical circulator is coupled, e.g. optically coupled, to a laser 104 via a first optical coupler 106, such that the optical circulator 107 receives laser light from the laser 104. The optical circulator 107 is configured to direct the laser light received from the laser 104 to the fluid detection fibre portions 110a, 110b, 110c, 110d. In other arrangements the optical circulator 107 can be replaced by an optical coupler, although this may incur increased light losses.

The fluid detection fibre portions 110a, 110b, 110c, 110d are similar to the fluid detection fibre portions 10a, 10b shown in FIG. 1 and each comprise a void 114 and an opening 116 into the void 114 that are similar to the void 14 and opening 16 described above.

The fluid detection fibre portions 110a, 110b, 110c, 110d may differ from the fluid detection fibre portions 10a, 10b by the inclusion of a partial reflector 115 arranged to reflect a portion of the light that has interacted with (e.g. passed through) the void 114 of the fluid detection fibre portion 110a, 110b, 110c, 110d back towards the optical circulator 107. In the arrangement shown in FIG. 3, the partial reflectors comprise Bragg gratings arranged within the fluid detection fibre portions 110a, 110b, 110c, 110d. However, in other arrangements, the partial reflectors may comprise a void in the fibre or may be created by a fibre end surface in a joint between optical fibres of the fluid detection fibre portions. For example, the partial reflector 115 of each fluid detection fibre portion 110a, 110b, 110c, 110d may be formed by a fibre end surface of the fluid detection fibre portion, e.g. at a connection with the next fluid detection fibre portion in the series arrangement 110 of fluid detection fibre portions.

As shown in FIG. 3, when the fluid detection fibre portions 110a, 110b, 110c, 110d are arranged in series, the fluid detection fibre portions may be arranged such that the voids 114 of the fluid detection fibre portion are spaced apart along the length of the series arrangement 110 of fluid detection fibre portions by substantially equal distances. For example, the voids 114 may be spaced apart by approximately 1 m or more than 1 m along the length of the series arrangement 110 of fluid detection fibre portions. Additionally or alternatively, the fluid detection fibre portions 110a, 110b, 110c, 110d may be configured such that the partial reflectors 115 of the fluid detection fibre portions are spaced apart along the length of the series arrangement 110 of fluid detection fibre portions by the same distance as each other. In other arrangements, the distances between one or more of the voids 114 may be different and/or the distances between one or more of the partial reflectors 115 may be different.

In the arrangement shown in FIG. 3, the fluid detection fibre portions 110a, 110b 110c, 110d are directly connected together to form the series arrangement 110 of fluid detection fibre portions. However, in other arrangements, lengths of optical fibre may be provided between one or more of the adjacent fluid detection fibre portions 110a, 110b, 110c, 110d. For example, a length of optical fibre may be provided between the second and third fluid detection fibre portions 110b, 110c in the series arrangement 110. The lengths of optical fibre provided between the fluid detection fibre portions may be the same length or may be different lengths.

The lengths of optical fibre may be provided between adjacent ones of the fluid detection fibre portions within the series arrangements of fluid detection fibre portions, so that the fluid detection fibre portions can be positioned in different locations at which is it desirable to detect fluid (such as a gas or liquid), with the locations being separated by the length of optical fibre. In this way, a single series arrangement of fluid detection fibre portions can extend between a plurality of locations for detecting fluid.

The optical circulator 107 is configured to direct the light received from the fluid detection fibre portions 110a, 110b, 110c, 110d towards a detector 130, which is similar to the detector 30 described above.

In the arrangement shown in FIG. 3, a reference fibre portion 120 is arranged between the laser 104 and the detector 130 in parallel with the optical circulator 107 and the fluid detection fibre portions 110a, 110b, 110c, 110d. The first optical coupler 106, or another optical coupler, is arranged to couple, e.g. optically couple, the reference fibre portion 120 to the laser 104, so that light from the laser is supplied to the reference fibre portion 120.

The reference fibre portion 120 and the optical circulator 107 are coupled, e.g. optically coupled, to an optical fibre 132 connected to the detector 130 by a second optical coupler 108. The light that has passed through the reference fibre portion 120 is thereby caused to interfere with the light that has interacted with (e.g. passed through) the voids 114 of each of the fluid detection fibre portions 110a, 110b, 110c, 110d and been reflected by the partial reflectors 115 in the fluid detection fibre portions 110, at or before reaching the detector 130.

In another arrangement of the disclosure, the reference fibre portion 120 may be arranged in series with the fluid detection fibre portions 110a, 110b, 110c, 110d. For example, the reference fibre portion 120 may be provided on an opposite end of the fluid detection fibre portions 110a, 110*b*, 110*c*, 110*d* to the optical circulator 107, e.g. at the distal end of the series arrangement 110 of fluid detection fibre portions. When the reference fibre portion 120 is arranged in series with the fluid detection fibre portions, the reference fibre portion 120 may comprise a reflector, e.g. a partial or total reflector, such as a Bragg grating, to reflect at least a portion of the light passing through the reference fibre portion 120 back to the optical circulator 107.

As described above, light that has interacted with fluid in the void 114 of one of the fluid detection fibre portions 110*a*, 110*b*, 110*c*, 110*d* may be reflected back to the optical circulator 107 by the partial reflector 115 provided in the corresponding fluid detection fibre portion 110*a*, 110*b*, 110*c*, 110*d*. Because the partial reflectors 115 are spaced apart along the length of the series arrangement 110 of the fluid detection fibre portions, the light that has interacted with the voids 114 of different ones of the fluid detection fibre portions 110*a*, 110*b*, 110*c*, 110*d* travels a different distance from the laser 104 before reaching the detector 130. Light that has interacted with each void 114 therefore interferes with the light from the reference fibre portion 120 with a different optical path length difference compared to light that has interacted with the void 114 of a different one of the fluid detection fibre portions 110*a*, 110*b*, 110*c*, 110*d*.

Portions of the interferometric signal relating to the portions of light that have interacted with each of the voids 114 of the fluid detection fibre portions 110*a*, 110*b*, 110*c*, 110*d* may therefore be distinguished from one another using the RRI technique in the same way as in the arrangement shown in FIG. 1.

The laser 104 and the detector 130 may be provided within an interrogation unit 102 of the interferometric fluid sensing system. Additionally, one or more controllers, such as a system controller, or a laser controller 140 and a detector controller 142 may be provided in the interrogation unit 102 for controlling the operation of the laser 104 and the detector 130.

As depicted in FIG. 3, the first optical coupler 106, the optical circulator 107 and the second optical coupler 108 may also be provided in the interrogation unit 102. In some arrangements, the reference fibre portion 120 providing the reference arm for the interferometers may also be provided in the interrogation unit 102.

The fluid detection fibre portions 110*a*, 110*b*, 110*c*, 110*d* may be optically coupled to the interrogation unit 102, e.g. the optical circulator 107 of the interrogation unit 102, by a length of optical fibre 103. The length of optical fibre 103 may be any desirable length. In this way, the fluid detection fibre portions 110*a*, 110*b*, 110*c*, 110*d* may be installed at a location where it is desirable to detect fluid that is remote from the interrogation unit 102. The components provided within the interrogation unit 102 may be provided within a common housing. Alternatively, the interrogation unit 102 may comprise a plurality of housings for housing different ones of the components.

Figure 4:
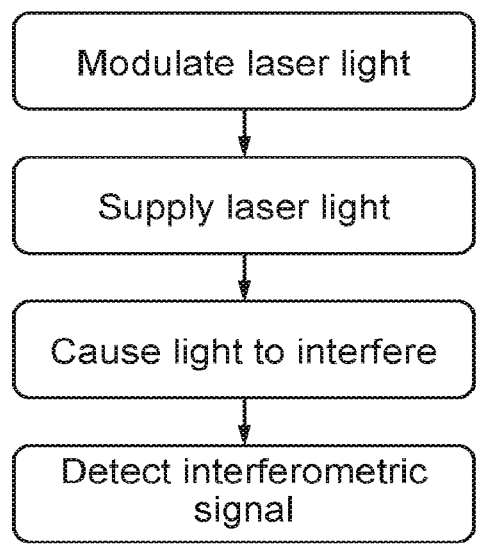
FIG. 4 is a flow chart illustrating an interferometric fluid detection method, according to arrangements of the present disclosure.

With reference to FIG. 4, an interferometric fluid detection method 400 may be used to detect the presence of fluid (such as gas or liquid) at a plurality of locations, by using the interferometric fluid sensing system 2, 100 shown in FIG. 1 or 3. The method 400 may be performed by the laser and detector controllers 40, 140, 42, 142 or a system controller configured to control both of the laser 4, 104 and the detector 30, 130.

The method 400 comprises a first step 402, in which laser light is generated by the laser 4, 104. The laser 4, 104 may be a low power laser and the light coupled into the fibre may have a power of less than or equal to 35 mW. The wavelength of light being produced by the laser is varied with time through a range of wavelengths, e.g. according to a first function. The range of wavelengths may be an absorption range of wavelengths that includes a value of wavelength at which the fluid to be detected is able to absorb energy from light passing through it.

The interferometric fluid detection system may be configured to detect fluids, such as hydrocarbons, e.g. ethane, methane, propane, ethylene and acetylene, hydrogen sulphide or any other gas or liquid that absorbs light passing through it. The absorption range may be selected according to the properties of the fluid or fluids to be detected.

The wavelength of the laser light may be varied through the absorption range of wavelengths following a ramped or saw tooth waveform, e.g. a linear ramped or saw tooth profile. Alternatively, the wavelength may be varied through the absorption range of wavelengths following a non-linear waveform. The wavelength of the light may be varied such that the wavelength of the light varies repeatedly, e.g. cycles, through the absorption range, e.g. at a first frequency.

The laser light is further modulated in the first step 402 by applying a sinusoidal wavelength modulation to the variation in wavelength, e.g. by superimposing the variation in wavelength onto a sinusoidal carrier function. The sinusoidal variation in wavelength introduced by the sinusoidal wavelength modulation may have a smaller amplitude than the absorption range. Additionally, a frequency of the sinusoidal modulation, e.g. a second frequency, may be greater than the frequency at which the wavelength of light is varied through the absorption range, e.g. the first frequency. For example, the first frequency may be between 1 Hz and 10 Hz and the second frequency may be between 10 kHz and 100 kHz.

As described above, by applying a sinusoidal wavelength modulation to the light being produced by the laser 4, 104, RRI techniques can be used to distinguish between the light passing through the voids 14, 114 of each of the fluid detection fibre portions 10*a*, 10*b*, 110*a*, 110*b*, 110*c*, 110*d*, based on the OPDs of their interferences with light from the reference fibre portion 20, 120.

The laser 4, 104 may be one that is capable of modulating the wavelength of light emitted from the laser. The light from the laser 4, 104 may be modulated using any desired method. For example, the laser 4, 104 may comprise a laser diode, e.g. an injection laser diode, and the laser controller 40, 140 may modulate an injection current provided to the laser 4, 104 in order to control the wavelength of light produced by the laser to generate the modulated laser light. Modulation of the laser light in this way is described in more detail with reference to FIGS. 7*a* to 7*d* below.

The method 400 comprises a second step 404, in which the modulated laser light is supplied to the plurality of fluid detection fibre portions 10*a*, 10*b*, 110*a*, 110*b*, 110*c*, 110*d* and the reference fibre portion 20, 120.

The method 400 comprises a third step 406, in which the laser light that interacts with fluid in the void 14, 114 of each fluid detection fibre portion 10*a*, 10*b*, 110*a*, 110*b*, 110*c*, 110*d* is caused to interfere with the light passing through the reference fibre portion 20, 120, and a fourth step 408, in which the interferometric signal resulting from the interference of light from the fluid detection fibre portions and reference fibre portion is detected using the detector 30, 130.

The interferometric signal is processed using an RRI technique in order to distinguish between the portions of the interferometric signal corresponding to the interference of light that has interacted with the voids 14, 114 of each of the fluid detection fibre portions 10*a*, 10*b*, 110*a*, 110*b*, 110*c*, 110*d* with the light that has passed through the reference fibre portion 20, 120. In particular, real and imaginary parts of the interferometric signal may be multiplied by a window function, such as a Gaussian window function. The windowed signals may then be multiplied by the real and imaginary parts of notional interferometric signals expected from interferometers having OPDs corresponding to the OPDs of interferences between light passing through, or being reflected within, each of the fluid detection fibre portions 10*a*, 10*b*, 110*a*, 110*b*, 110*c*, 110*d* and the light passing through the reference fibre portion 20, 120. The result of each multiplication is then processed to determine the intensity and interferometric phase of each portion of the signal.

Figure 5A:
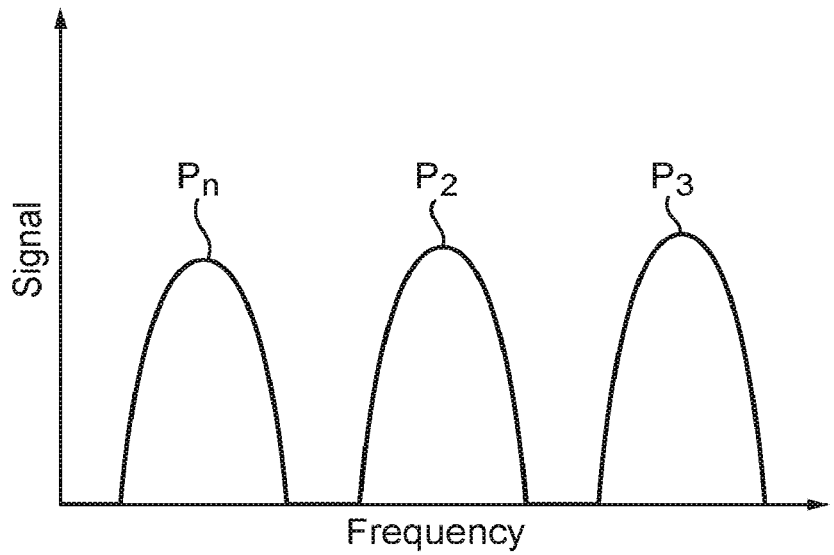
FIGS. 5a and 5b are graphs showing examples of simplified frequency spectra of interferometric signals received by a detector of the interferometric fluid sensing system in FIG. 1, with and without the presence of a fluid.
Figure 5B:
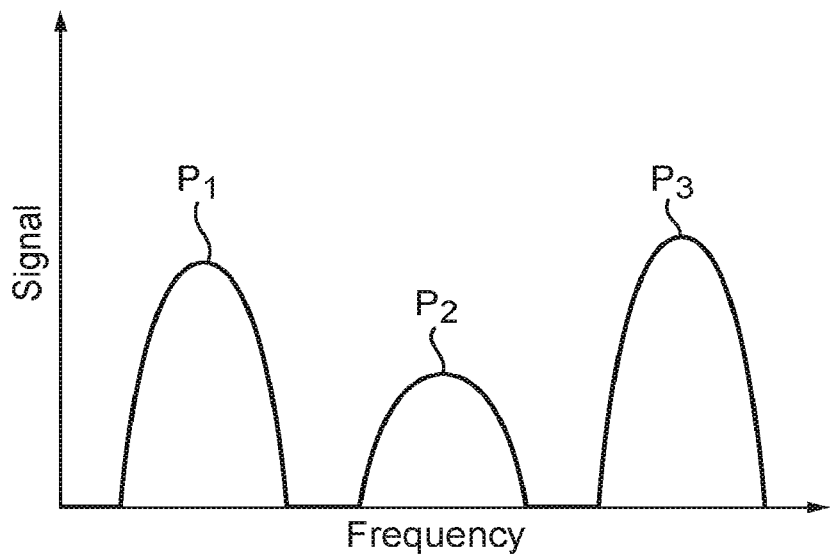

FIGS. 5*a* and 5*b* show examples of interferometric signals from an interferometric fluid sensing system comprising three fluid detection fibre portions. The signals have been multiplied by a Gaussian window function and transformed into the frequency domain, e.g. by performing Fourier transforms on the signals. FIG. 5*a*, shows a signal detected when no fluid was present in any of the voids of the fluid detection fibre portions. As shown, first, second and third peaks P1, P2, P3 correspond to portions of the interferometric signal relating to each (in the arrangement with three fluid detection fibre portions) fluid detection fibre portion and are separated in frequency by values corresponding to the differences in OPD of the corresponding interferences.

FIG. 5*b* shows a signal detected when no fluid was present in the voids of the first and third fluid detection fibre portions and a quantity of fluid was present in the void of the second fluid detection fibre portion. When fluid is present in the void of a fluid detection fibre portion, light passing through the void is absorbed by the fluid at the fluid absorption wavelength, thereby reducing the intensity of the light. Accordingly, a signal magnitude of the second peak P2, which corresponds to the second fluid detection fibre portion, is smaller than signal magnitudes of the first and third peaks P1, P3.

Furthermore, when light is absorbed by the fluid, the refractive index of the fluid may change, which may affect the phase of the light passing through the fluid and in turn affect the interferometric phase of the portion of the interferometric signal corresponding to the fluid detection fibre portion in which fluid is present. Hence, determining the interferometric phase information of the portions of the interferometric signal corresponding to each fluid detection fibre portion provides a further indication of the presence of fluid within the voids.

As the light passes through the optical fibres, e.g. the fluid detection fibre portions 10*a*, 10*b*, 110*a*, 110*b*, 110*c*, 110*d*, and other optical components arranged between the laser 4, 104 and the detector 30, 130, the polarisation of the light may change. For example, the polarisation of the light may change due to bends in the optical fibres. Changes in the polarisation of the light can result in changes in the intensity of a resulting interferometric signal, or portions of the interferometric signal. This phenomenon is known as Polarisation Induced signal Fading (PIF).

With reference to FIG. 6*a*, in order to account for the effect of (PIF), an interferometric fluid sensing system 600*a* may comprise a further reference fibre portion 610, configured to provide a further reference arm of the interferometric system, and a further detector 620.

The further reference fibre portion 610 is coupled to the laser 104, e.g. by a third optical coupler 606. The further reference fibre portion 610 is also optically coupled to the further detector 620. As shown in FIG. 6*a*, each of the fluid detection fibre portions 110*a*, 110*b*, 110*c*, 110*d* is optically coupled to the further detector 620, in addition to the detector 130, such that light from the fluid detection fibre portions 110*a*, 110*b*, 110*c*, 110*d* interferes with the light from the further reference fibre portion 610 at or before reaching the further detector 620.

The interferometric fluid sensing system 600*a* includes one or more fourth optical couplers 608 for optically coupling the fluid detection fibre portions 110*a*, 110*b*, 110*c*, 110*d* to the further detector 620, e.g. to an optical fibre 622 coupled to the further detector 620. The further reference fibre portion 610 is thereby connected between the laser 104 and the further detector 620 in parallel with the fluid detection fibre portions 110*a*, 110*b*, 110*c*, 110*d*.

The further reference fibre portion 610 may be the same length, e.g. have the same optical path length, as the reference fibre portion 120, or may be a different length. The interferometric fluid sensing system 600*a* may otherwise be the same as the interferometric fluid sensing system 100 described above.

Although in the arrangement shown in FIG. 6*a*, the fluid detection fibre portions 110*a*, 110*b*, 110*c*, 110*d* are connected in series, in other arrangements, the fluid detection fibre portions may be connected in parallel with one another between the laser 104, and the detector 130 and further detector 620.

The interferometric fluid sensing system 600*a* is configured such that the polarisation of light passing through the further reference fibre portion 610 is orthogonal to the polarisation of light passing through the reference fibre portion 120. The interferometric fluid sensing system 600*a* may comprise a polarisation controller configured to control the polarisation of the light passing through the reference fibre portion 120 and the further reference fibre portion 610. Alternatively, as depicted in FIG. 6*a*, the interferometric fluid sensing system 600*a* may comprise an optical component, such as a wave plate 612, configured to rotate the polarisation of light being supplied to the further reference fibre portion 610 by 90 degrees.

Because the polarisations of the light passing through the reference fibre portion and further reference fibre portions are orthogonal, light from the fluid detection fibre portions will interfere with the light passing through either one or both of the reference fibre portion and further reference fibre portion regardless of its polarisation. Hence, by appropriately combining light intensity and interferometric phase information from the interferometric signals received at detector 130 and further detector 620, the effect of PIF may be accounted for.

Figure 6B:
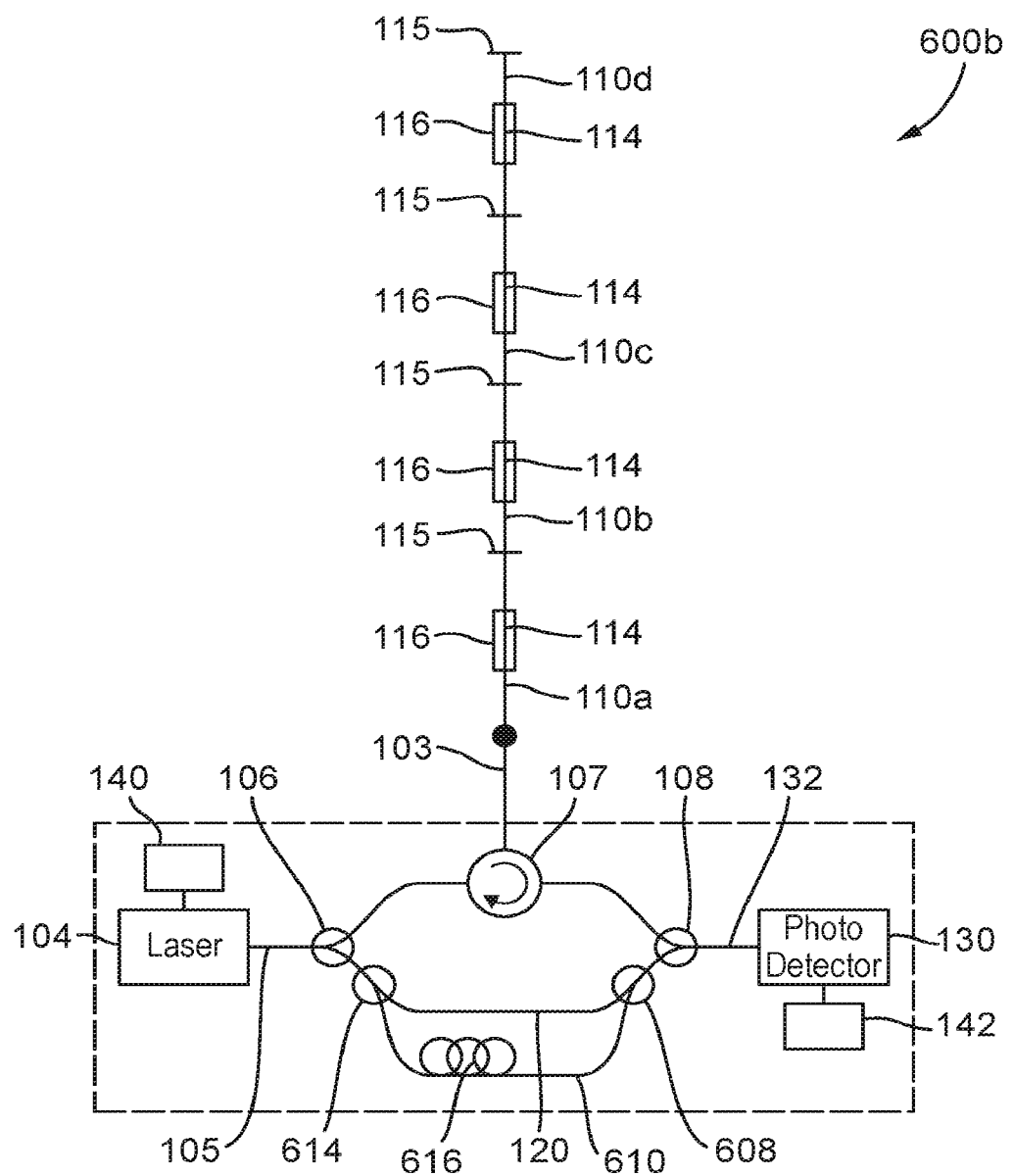

An alternative interferometric fluid sensing system 600*b* to the above described polarisation-sensitive interrogation that does not require an additional detector 620 and associated signal processing is shown in FIG. 6*b*. Here, light is separated into two orthogonal polarisation directions by a polarising beam-splitter or fibre polarisation splitter 614, with the orthogonal outputs forming the reference arm 120 and a further reference arm 610, where the polarisation of reference arms 120 and 610 is maintained constant, for example using polarisation-maintaining fibre, before they are recombined using coupler 608. Light coming from coupler 608 is then combined with the light from the first fibre portions using coupler 108. An additional delay line 616 included in reference arm 610 and introduces a path difference between the reference arms 120 and 610. This path difference is then used to uniquely identify the interference signals that result from interference between the fluid fibre portions 110 and the reference fibre portion 120, with signals corresponding to one set of path-lengths for fluid fibre portion 110 interrogated at one polarisation direction, and the signals that result from interference between the fluid fibre portions 110 and the additional reference fibre portion 610, with signals corresponding to further set of path-lengths, offset from the other set, for the fluid fibre portions 110 interrogated at the orthogonal polarisation.

As described above, the laser 4, 104 may comprise a laser diode, e.g. an injection laser diode. Laser diodes have multiple advantages compared to other forms of laser in terms of size, complexity and cost. Furthermore, the wavelength of light produced by a laser diode can be controlled by controlling the injection current supplied to the diode. This makes laser diodes particularly suitable for systems making use of RRI techniques, because sinusoidal wavelength modulation can be applied to the laser light by modulating the current supplied to the laser diode, however, the disclosed invention is not limited to injection laser diodes and could also be realised with other types of lasers that allow wavelength modulation, such as a cascade laser.

Figure 7A:
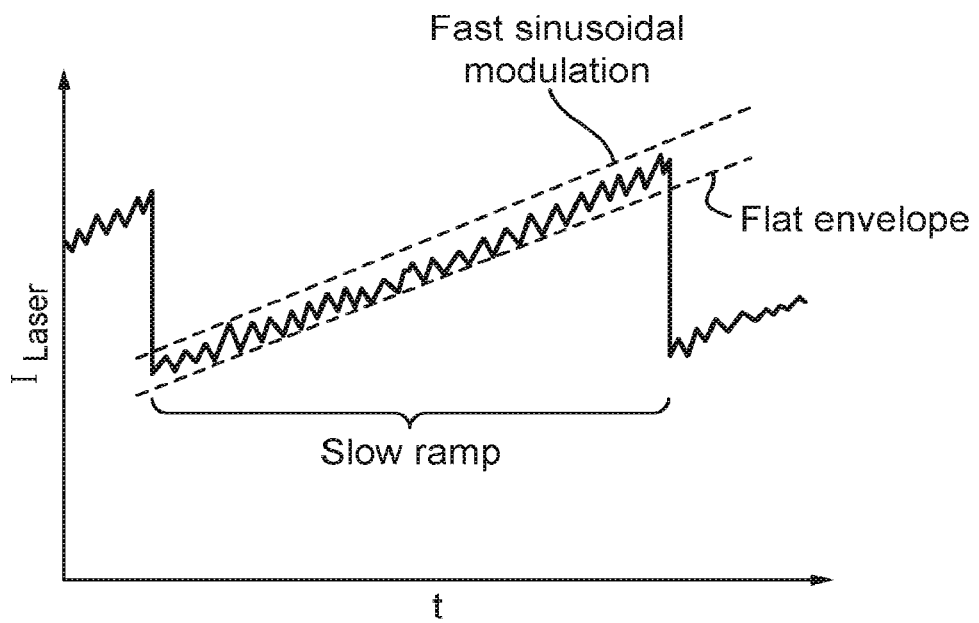
FIGS. 7a, 7b, 7c and 7d are graphs that are useful for understanding the effect of current pre-shaping on the operation of the laser of the interferometric fluid sensing system.
Figure 7B:
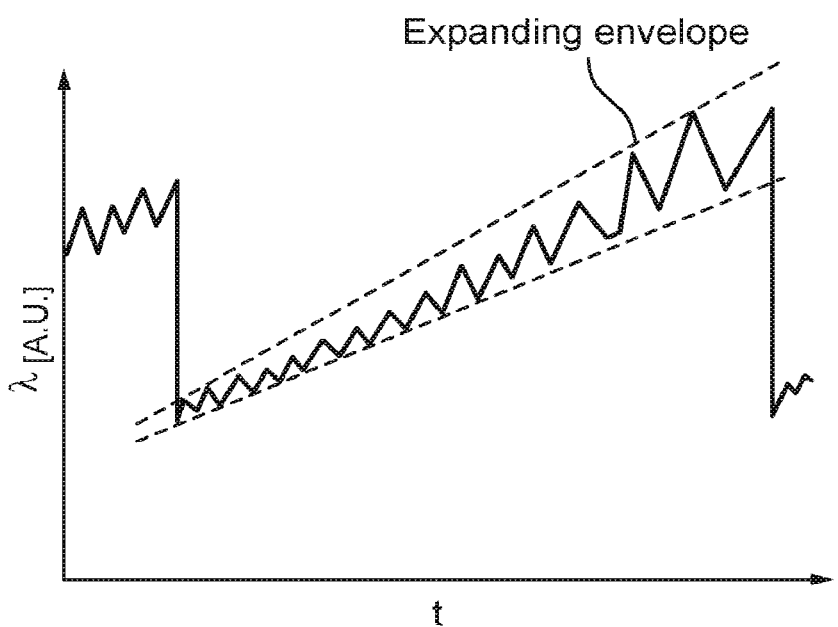
Figure 7C:
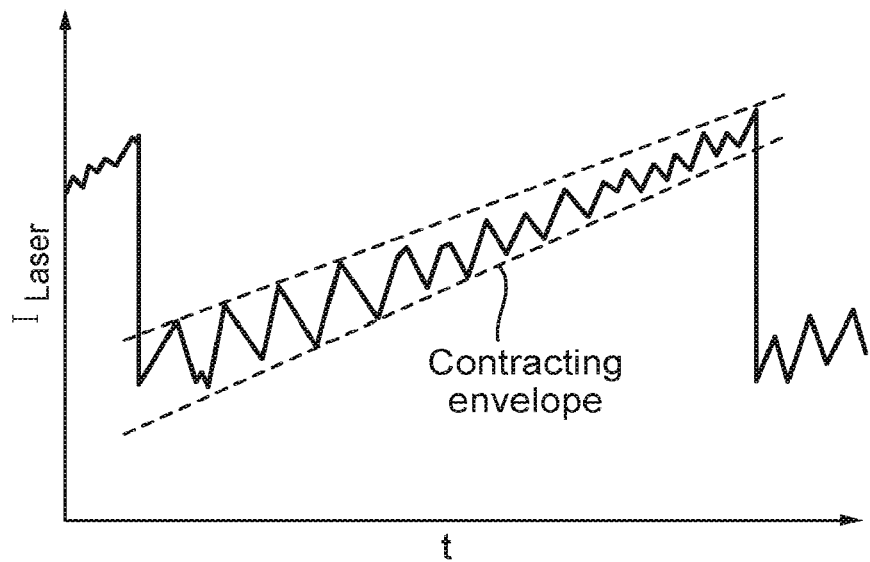
Figure 7D:
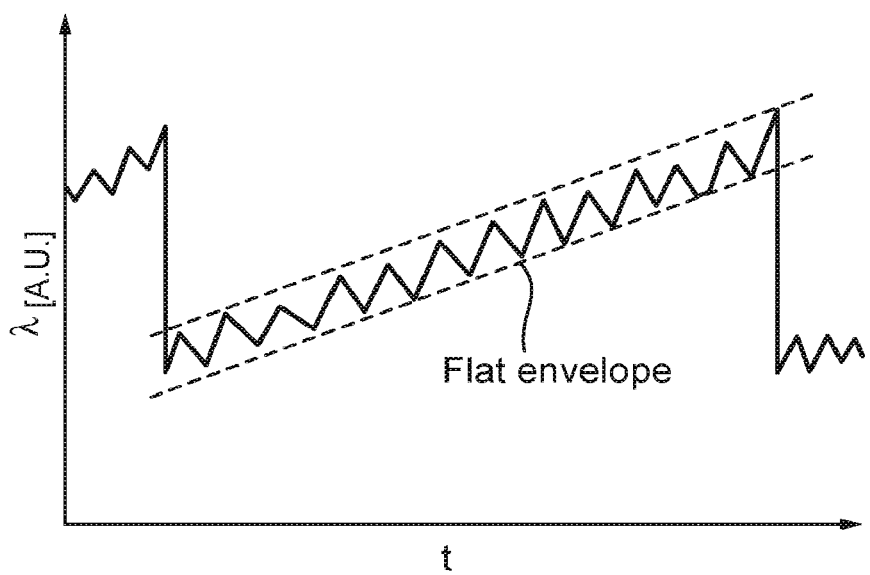

FIGS. 7a to 7d are graphs showing the variations in wavelength of laser light produced by a laser diode when particular variations in current are supplied to the laser diode. More particularly, FIG. 7b shows the variation in wavelength of the laser light produced by a laser diode when the current supplied to the laser diode is varied in the way shown in FIG. 7a, and FIG. 7d shows the variation in wavelength of the laser light produced by a laser diode when the current supplied to the laser diode is varied in the way shown in FIG. 7c.

As described above, it may be desirable to vary the wavelength of laser light, such that the laser light varies through the absorption range and by applying a sinusoidal modulation to this variation. However, as shown in FIGS. 7a and 7b, if the current supplied to the laser diode is varied in this way, the amplitude of the sinusoidal variations in wavelength introduced by the modulation may vary as the wavelength of the laser light varies through the absorption range. In particular, as shown in FIG. 7b, the amplitude of the sinusoidal variations in wavelength may increase as the wavelength of laser light increases through the absorption range. This effect is due to the properties of the laser diode and the relationship between current supplied to the diode and wavelength of laser light produced. The variation in the amplitude of the sinusoidal variation may differ depending on the particular laser diode being used.

With reference to FIG. 7c, in order to provide a desired variation in wavelength of the laser light, the current supplied to the laser diode may be pre-shaped, e.g. by varying the amplitude of the sinusoidal carrier function as the current supplied to the laser is varied, e.g. between minimum and maximum values. For example, as shown in FIG. 7c, the amplitude of the sinusoidal carrier function may be reduced as the current being supplied to the laser is increased. As depicted in FIG. 7d, pre-shaping the current in this way allows the wavelength of light generated by the laser diode to be varied in the desired way, e.g. such that the amplitude of the superimposed sinusoidal variations resulting from the sinusoidal modulation is substantially constant as the wavelength varies through the absorption range.

Figure 8A:
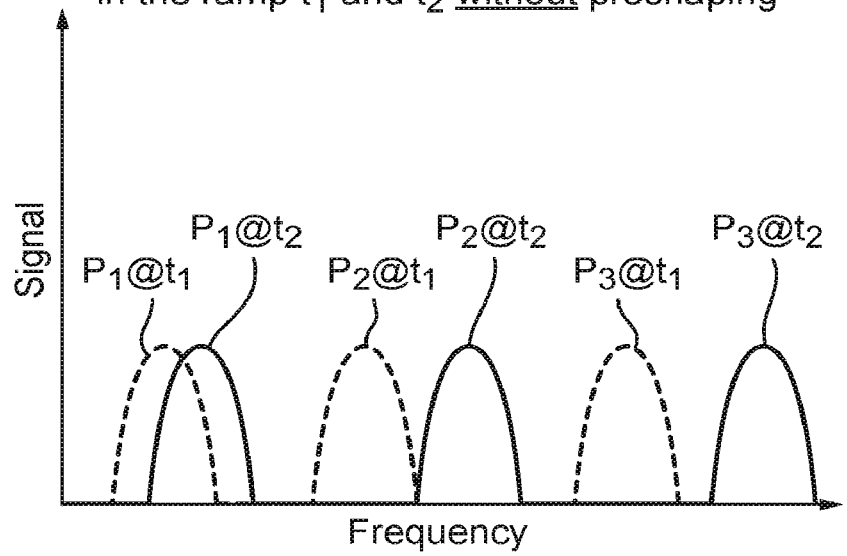
Figure 8A:
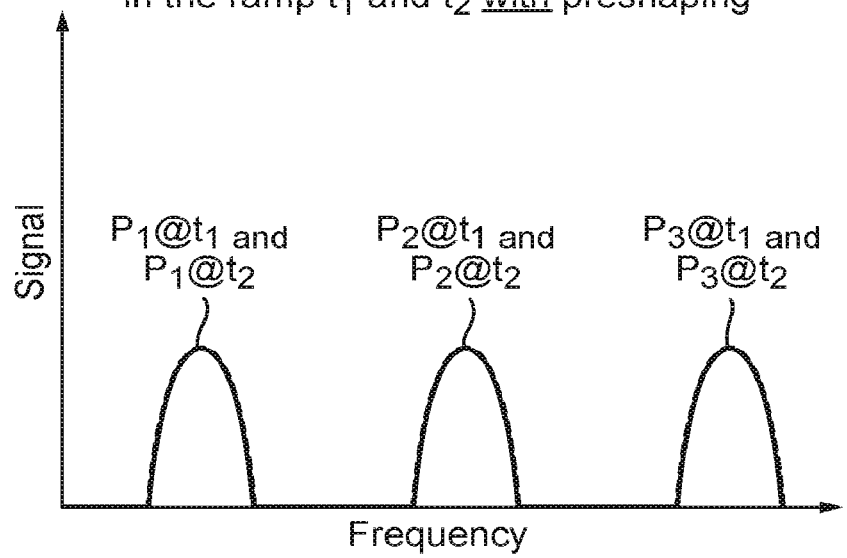

FIGS. 8a and 8b show examples of Fourier transforms of interferometric signals from an interferometric fluid sensing system comprising three fluid detection fibre portions, illustrating the benefits of current pre-shaping. In FIGS. 8a and 8b, peaks $P_1@t_1$, $P_2@t_1$ correspond to portions of the interferometric signal relating to first and second fluid detection fibre portions respectively at time $t_1$ and peaks $P_1@t_2$, $P2@t_2$ correspond to portions of the interferometric signal relating to the first and second fluid detection fibre portions respectively at time $t_2$, with no fluid being present within the voids of the first and second fluid detection fibre portions at time $t_1$ or $t_2$.

In the example shown in FIG. 8a, the current being supplied to the laser was varied in the way depicted in FIG. 7a. In other words, no pre-shaping was applied to the current. Hence, the wavelength of light generated by the laser varied substantially as depicted in FIG. 7b. As depicted in FIG. 8a, because the amplitude of the superimposed sinusoidal modulation of wavelength varied, the frequencies of the portions of the interferometric signal have also varied. In other words, the change in amplitude of the superimposed sinusoidal variations in wavelength has had the effect of changing the apparent OPD of the interferometric signal. When the frequency of the portions of the interferometric signal varies in this way, the process of separating the portions of the interferometric signal relating to the different fluid detection fibre portions and determining the intensity and interferometric phase of the different portions of the interferometric signal becomes more complex.

In the example shown in FIG. 8b, pre-shaping was applied to the current being supplied to the laser diode, such that the current being supplied to the laser was varied in the way depicted in FIG. 7c. The wavelength of light generated by the laser therefore varied substantially as depicted in FIG. 7d. As depicted in FIG. 8b, the peaks corresponding to the interferometric signal relating to first and second fluid detection fibre portions respectively at times $t_1$ and $t_2$ are at the same frequency. Processing of the interferometric signal shown in FIG. 8b using RRI techniques is therefore less complex than processing of the interferometric signal shown in FIG. 8a.

The aforementioned system or method may detect one particular, e.g. pre-determined, fluid (e.g. gas or liquid). Alternatively, the system may be configured to determine the presence of a particular fluid from a number of different fluids, e.g. by linking a determined absorption feature with the particular fluid. However, if there are other fluids that the target fluid can be confused with, then the unique identification may require additional lasers that operate simultaneously at different wavelengths using different absorption features of the target fluid. Alternatively, a swept laser with a wide wavelength range could be used that covers enough of the spectrum to be confident that several absorption features of the target fluid can be measured. Such a swept laser would also offer the possibility of simultaneously measuring several fluids.

Figure 9:
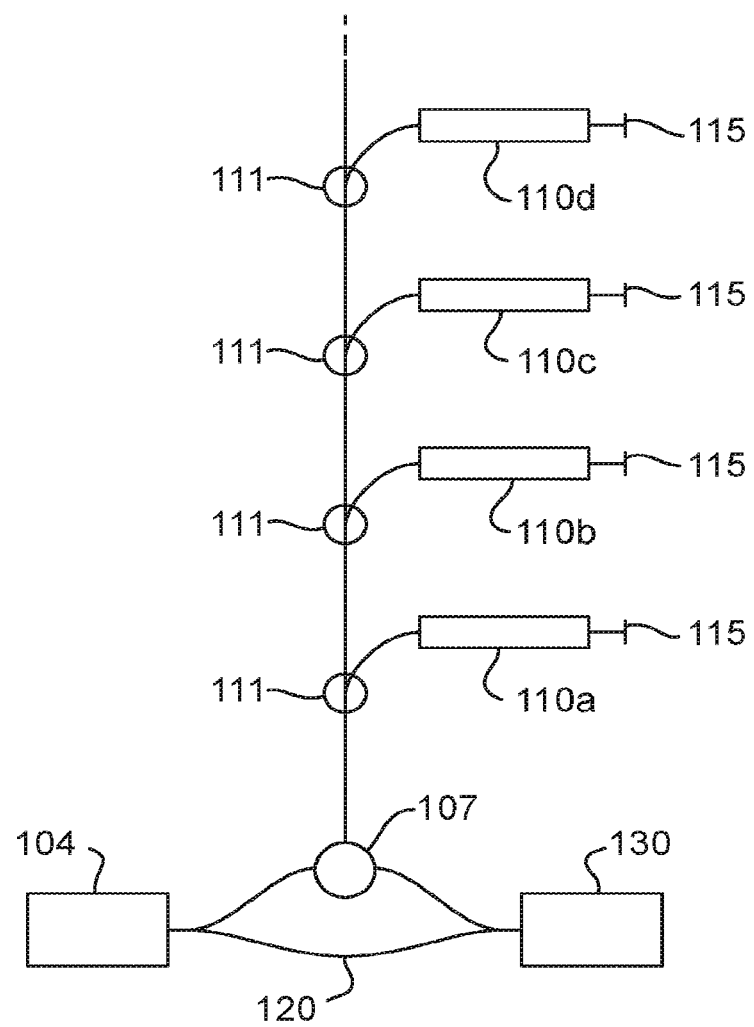
FIG. 9 is a schematic view of another interferometric fluid sensing system, according to arrangements of the present disclosure.

Referring to FIG. 9, in another arrangement an interferometric fluid sensing system 900 may comprise fluid detection fibre portions 110a, 110b, 110c, 110d arranged in a branched network. The fluid detection fibre portions 110a, 110b, 110c, 110d may branch from a main fibre at successive locations spaced apart along the length of the main fibre. Although four fluid detection fibre portions are depicted, it will be appreciated that any number of fluid detection fibre portions may be provided. Reflectors 115 may be provided at the ends of each branch. Couplers 111 may be provided between each fluid detection fibre portion 110a, 110b, 110c, 110d and the main fibre. The arrangement may otherwise be similar to either of the arrangements depicted in FIGS. 3 and 6, e.g. with a reference fibre portion 120 arranged between laser 104 and detector 130 in parallel with the optical circulator 107 and the fluid detection fibre portions 110a, 110b, 110c, 110d. The system 900 may otherwise operate using the techniques described above.

The interferometric fluid detection system described above is advantageous in that the system can comprise a single fibre including multiple fluid detection fibre portions, e.g. formed from a single fibre or joined together to create a single fibre. The single fibre can then be arranged along the length of a fluid pipe or through an area in which it is desirable to detect the presence of fluid. An interferometric signal can then be interrogated to detect and location of fluid along the length of the single fibre.

This arrangement is more cost effective and practical than installing individual pellistors, semiconductor gas sensors or electrochemical devices at each of the locations of interest, or installing an optical system with multiple lasers, detectors and branches of optical fibres. It has the potential to provide greater coverage of such point based sensors, since (a) it is possible to multiplex a large number of fluid-detecting fibre portions within a single optical fibre cable without adding complexity to the interrogation system, and (b) there is potential for the system to provide complete coverage of fluid sensing along the entire length of an optical fibre cable comprising suitably arranged sensing portions.

Furthermore, the system is easy to calibrate by associating a particular location with a particular one of the fluid detection fibre portions provided on the system.

It will be appreciated by those skilled in the art that although the invention has been described by way of example, with reference to one or more exemplary examples, it is not limited to the disclosed examples and that alternative examples could be constructed without departing from the scope of the invention as defined by the appended claims.

The invention claimed is:

1. An interferometric fluid sensing system comprising:
a laser;
a plurality of first fibre portions arranged to receive laser light from the laser, wherein each of the first fibre portions is associated with a corresponding void into which fluid from the environment around the corresponding first fibre portion is free to enter, wherein the first fibre portions are configured such that at least a portion of the laser light received by each first fibre portion interacts with the fluid in the corresponding void;
a second fibre portion configured to provide a reference arm for the interferometric fluid sensing system; and
a detector arranged to receive light from the first and second fibre portions, wherein the system is configured such that the laser light that passes through each first fibre portion is caused to interfere with the light passing through the second fibre portion at or before reaching the detector, wherein
each of the first fibre portions is arranged such that that light passing through each first fibre portion travels from the laser to the detector over a different path length from the light passing through the other first fibre portions,
the system is configured such that the wavelength of light provided by the laser varies with time according to a first function, which varies through a range of wavelengths, superimposed onto a second, cyclical carrier function, and
two or more of the first fibre portions are arranged in series with one another.

2. The system of claim 1, wherein the second fibre portion is arranged between the laser and the detector in parallel or series with the plurality of first fibre portions.

3. The system of claim 1, wherein the first fibre portions comprise a partial reflector or a fibre boundary configured to reflect a portion of the light that has passed through the first fibre portion.

4. The system of claim 1, wherein the voids of the first fibre portions are spaced apart from one another along the length of the series arrangement of the first fibre portions by approximately 1 m or more than 1 m.

5. The system of claim 1, wherein two or more of the first fibre portions are arranged in parallel with one another between the laser and the detector.

6. The system of claim 1, wherein the wavelength of the laser light is modulated by varying a current supplied to the laser over time.

7. The system of claim 1, wherein the system further comprises:
a third fibre portion configured to provide a further reference arm of the interferometric fluid sensing system; and
a further detector arranged to receive light from the first and third fibre portions, wherein the system is configured such that the laser light that passes through each first fibre portion is caused to interfere with the light passing through the third fibre portion at or before reaching the further detector, and wherein the system is configured such that light passing through the third fibre portion is polarised orthogonally to the light passing through the second fibre portion.

8. The system of claim 1, wherein the system further comprises:
a third fibre portion configured to provide a further reference arm of the interferometric fluid sensing system;
wherein the system is configured such that the laser light that passes through each first fibre portion is caused to interfere with the light passing through the third fibre portion at or before reaching the further detector, and wherein the system is configured such that light passing through the third fibre portion is polarised orthogonally to the light passing through the second fibre portion and wherein the system is configured such that the second and third fibre portions differ in path length such that the light from each first fibre portion interfering with the second fibre portion can be distinguished from light of the first fibre portion interfering with the third fibre portion.

9. The system of claim 1, further comprising a controller configured to process a signal received by the detector using a range-resolved interferometry technique, in order to distinguish between the portions of the signal corresponding to light that has passed through each of the first fibre portions.

10. The system of claim 1, wherein the laser and detector are provided in an interferometric interrogation unit and wherein the first fibre portions are optically coupled to the interrogation unit.

11. The system of claim 10, wherein the second fibre portion is provided within the interferometric interrogation unit.

12. The system of claim 10, wherein the interferometric interrogation unit further comprises an optical circulator or coupler configured to direct light from the laser to the first fibre portions and direct light from the first fibre portions to the detector.

13. An interferometric fluid detection method, the method comprising:
generating laser light, such that the wavelength of the laser light varies according to a modulated function, the modulated function comprising a first function, which varies through a range of wavelengths, modulated by a second, cyclical carrier function;

supplying the modulated laser light to:
- a plurality of first fibre portions, wherein each of the first fibre portions is associated with a corresponding void into which fluid from the environment around the corresponding first fibre portion is free to enter, wherein the first fibre portions are configured such that at least a portion of the laser light received by each first fibre portion interacts with fluid in the corresponding void; and
- a second fibre portion configured to provide a reference arm;

causing the laser light that passes through each first fibre portion to interfere with the light passing through the second fibre portion;

detecting the interferometric signal resulting from the interference of light from the first and second fibre portions using a detector; and processing the interferometric signal using a range-resolved interferometry technique, in order to distinguish between the signals corresponding to light that has passed through the each of the first fibre portions.

14. The interferometric fluid detection method of claim 13, wherein the laser light is supplied by a laser diode and wherein modulating the laser light comprises varying a current supplied to the laser diode.

15. The interferometric fluid detection method of claim 14, wherein the current supplied to the laser diode is varied with time according to a a first function, which varies through a range of currents, superimposed onto a second, cyclical carrier function.

16. The interferometric fluid detection method of claim 15, wherein the current is varied such that the magnitude of variations in current due to the cyclical modulation of the current changes as the current is varied through the range of currents.

17. The interferometric fluid detection method of claim 13, wherein the method further comprises:
- supplying the modulated laser light to a third fibre portion to provide a further reference arm;
- arranging the polarisation of the laser light supplied to the second and/or third fibre portions such that the polarisation of light passing through the third fibre portion is orthogonal to the laser light passing through the second fibre portion;
- causing the laser light that passes through each first fibre portion to interfere with the light passing through the third fibre portion;
- detecting the interferometric signal resulting from the interference of the light from the first and third fibre portions using a further detector.

18. The interferometric fluid detection method of claim 13, wherein the method further comprises:
- determining whether a fluid is present in the void of a particular first fibre portion based on an intensity and/or interferometric phase of a portion of the interferometric signal corresponding to light that has passed through the particular first fibre portion.

19. An interferometric fluid sensing system comprising:
a laser;
a plurality of first fibre portions arranged to receive laser light from the laser, wherein each of the first fibre portions is associated with a corresponding void into which fluid from the environment around the corresponding first fibre portion is free to enter, wherein the first fibre portions are configured such that at least a portion of the laser light received by each first fibre portion interacts with the fluid in the corresponding void;
a second fibre portion configured to provide a reference arm for the interferometric fluid sensing system;
a third fibre portion configured to provide a further reference arm of the interferometric fluid sensing system;
a detector arranged to receive light from the first and second fibre portions, wherein the system is configured such that the laser light that passes through each first fibre portion is caused to interfere with the light passing through the second fibre portion at or before reaching the detector, and
a further detector arranged to receive light from the first and third fibre portions, wherein the system is configured such that the laser light that passes through each first fibre portion is caused to interfere with the light passing through the third fibre portion at or before reaching the further detector, and wherein the system is configured such that light passing through the third fibre portion is polarised orthogonally to the light passing through the second fibre portion, wherein each of the first fibre portions is arranged such that that light passing through each first fibre portion travels from the laser to the detector over a different path length from the light passing through the other first fibre portions, and the system is configured such that the wavelength of light provided by the laser varies with time according to a first function, which varies through a range of wavelengths, superimposed onto a second, cyclical carrier function.

20. An interferometric fluid sensing system comprising:
a laser;
a plurality of first fibre portions arranged to receive laser light from the laser, wherein each of the first fibre portions is associated with a corresponding void into which fluid from the environment around the corresponding first fibre portion is free to enter, wherein the first fibre portions are configured such that at least a portion of the laser light received by each first fibre portion interacts with the fluid in the corresponding void;
a second fibre portion configured to provide a reference arm for the interferometric fluid sensing system; and
a third fibre portion configured to provide a further reference arm of the interferometric fluid sensing system;
a detector arranged to receive light from the first and second fibre portions, wherein the system is configured such that the laser light that passes through each first fibre portion is caused to interfere with the light passing through the second fibre portion at or before reaching the detector, wherein each of the first fibre portions is arranged such that that light passing through each first fibre portion travels from the laser to the detector over a different path length from the light passing through the other first fibre portions, the system is configured such that:

the wavelength of light provided by the laser varies with time according to a first function, which varies through a range of wavelengths, superimposed onto a second, cyclical carrier function, the laser light that passes through each first fibre portion is caused to interfere with the light passing through the third fibre portion at or before reaching the further detector, and the light passing through the third fibre portion is polarised orthogonally to the light passing through the second fibre portion and wherein the system is configured such that the second and third fibre portions differ in path length such that the light from each first fibre portion interfering with the second fibre portion can be distinguished from light of the first fibre portion interfering with the third fibre portion.

21. An interferometric fluid sensing system comprising:
a laser;
a plurality of first fibre portions arranged to receive laser light from the laser, wherein each of the first fibre portions is associated with a corresponding void into which fluid from the environment around the corresponding first fibre portion is free to enter, wherein the first fibre portions are configured such that at least a portion of the laser light received by each first fibre portion interacts with the fluid in the corresponding void;
a second fibre portion configured to provide a reference arm for the interferometric fluid sensing system;
a detector arranged to receive light from the first and second fibre portions, wherein the system is configured such that the laser light that passes through each first fibre portion is caused to interfere with the light passing through the second fibre portion at or before reaching the detector, wherein each of the first fibre portions is arranged such that that light passing through each first fibre portion travels from the laser to the detector over a different path length from the light passing through the other first fibre portions, and the system is configured such that the wavelength of light provided by the laser varies with time according to a first function, which varies through a range of wavelengths, superimposed onto a second, cyclical carrier function, and
a controller configured to process a signal received by the detector using a range-resolved interferometry technique, in order to distinguish between the portions of the signal corresponding to light that has passed through each of the first fibre portions.

22. An interferometric fluid detection method, the method comprising:
generating laser light, such that the wavelength of the laser light varies according to a modulated function, the modulated function comprising a first function, which varies through a range of wavelengths, modulated by a second, cyclical carrier function;
supplying the modulated laser light to:
a plurality of first fibre portions, wherein each of the first fibre portions is associated with a corresponding void into which fluid from the environment around the corresponding first fibre portion is free to enter, wherein the first fibre portions are configured such that at least a portion of the laser light received by each first fibre portion interacts with fluid in the corresponding void;
a second fibre portion configured to provide a reference arm; and
a third fibre portion configured to provide a further reference arm;
causing the laser light that passes through each first fibre portion to interfere with the light passing through the second fibre portion;
detecting the interferometric signal resulting from the interference of light from the first and second fibre portions using a detector; and
arranging the polarisation of the laser light supplied to the second and/or third fibre portions such that the polarisation of light passing through the third fibre portion is orthogonal to the laser light passing through the second fibre portion;
causing the laser light that passes through each first fibre portion to interfere with the light passing through the third fibre portion;
detecting the interferometric signal resulting from the interference of the light from the first and third fibre portions using a further detector.

* * * * *